US009456588B2

(12) United States Patent
Chan et al.

(10) Patent No.: US 9,456,588 B2
(45) Date of Patent: Oct. 4, 2016

(54) TRANSGENIC MOUSE HAVING A GENOME COMPRISING A HOMOZYGOUS DISRUPTION OF THE ENDOGENOUS MFN2 GENE EXPRESSION IN THE DOPAMINERGIC NEURONS

(71) Applicant: CALIFORNIA INSTITUTE OF TECHNOLOGY, Pasadena, CA (US)

(72) Inventors: David C. Chan, Arcadia, CA (US); Anh H. Pham, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 10 days.

(21) Appl. No.: 13/924,490

(22) Filed: Jun. 21, 2013

(65) Prior Publication Data

US 2013/0347135 A1 Dec. 26, 2013

Related U.S. Application Data

(60) Provisional application No. 61/662,523, filed on Jun. 21, 2012.

(51) Int. Cl.
*A01K 67/027* (2006.01)
*C12N 9/14* (2006.01)

(52) U.S. Cl.
CPC ....... *A01K 67/0275* (2013.01); *A01K 67/0276* (2013.01); *C12N 9/14* (2013.01); *A01K 2217/075* (2013.01); *A01K 2217/206* (2013.01); *A01K 2227/105* (2013.01); *A01K 2267/0318* (2013.01)

(58) Field of Classification Search
CPC ..................... A01K 67/0275; A01K 67/0276; A01K 2217/075; A01K 2217/206; A01K 2227/105; A01K 2267/0318; C12N 9/14
See application file for complete search history.

(56) References Cited

U.S. PATENT DOCUMENTS

2014/0024066 A1 1/2014 Chan et al.

OTHER PUBLICATIONS

Polejaeva and Mitalipov. "Stem cell potency and the ability to contribute to chimeric organisms." Reproduction. (Mar. 7, 2013);145(3):pp. R81-R88.*
Brevini et al. "Porcine embryonic stem cells: Facts, challenges and hopes."Theriogenology. (2007);68 (1) : pp. S206-S213.*
Rogers et al. "Disruption of the CFTR Gene Produces a Model of Cystic Fibrosis in Newborn Pigs." Science. Sep. 26, 2008; 321(5897): 1837-1841.*
Gerlai R. "Gene-targeting studies of mammalian behavior: is it the mutation or the background genotype?"Trends Neurosci. May 1996;19(5):177-81.*
Ozato et al. "Response to Comment on "Gene Disruption Study Reveals a Nonredundant Role for TRIM21/Ro52 in NF-κB-Dependent Cytokine Expression in Fibroblasts"". The Journal of Immunology (2009). vol. 183. No. 12. pp. 7620-7621.*
Speakman et al. "The contribution of animal models to the study of obesity."Lab Anim. Oct. 2008;42(4):413-32.*
Luisis et al. "The problem of passenger genes in transgenic mice." Arterioscler Thromb Vasc Biol. Oct. 2007;27(10):2100-3.*
Ammari, R et al.; "A Mouse Juvenile or Adult Slice With Preserved Functional Nigro-Striatal Dopaminergic Neurons"; Neuroscience; 159; 2009; pp. 3-6.
Bäckman, Cristina M. et al; "Characterization of a Mouse Strain Expressing Cre Recombinase From the 3' Untranslated Region of the Dopamine Transporter Locus"; Genesis; 44; 2006; pp. 383-390.
Beurrier, C. et al.; "Preservation of the Direct and Indirect Pathways in an In Vitro Preparation of the Mouse Basal Ganglia"; Neuroscience; 140; 2006; pp. 77-86.
Chen, Hsiuchen et al.; "Mitofusins Mfn1 and Mfn2 coordinately regulate mitochondrial fusion and are essential for embryonic development"; The Journal of Cell biology; vol. 160; No. 2; Jan. 20, 2003; pp. 189-200.
Chen, Hsiuchen et al.; "Mitochondrial Fusion Protects against Neurodegeneration in the Cerebellum"; Cell; 130; Aug. 10, 2007; pp. 548-562.
Cheng, Hsiao-Chun et al.; "Clinical Progression in Parkinson Disease and the Neurobiology of Axons"; Ann Neurol; 67; 2010; pp. 715-725.
Damier, P. et al.; "The substantia nigra of the human brain: II. Patterns of loss of dopamine-containing neurons in Parkinson's disease"; Brain ; 122; 1999; pp. 1437-1448.
Hirsch, Etienne et al.; "Melanized dopaminergic neurons are differentially susceptible to degeneration in Parkinson's disease"; Nature; vol. 334; Jul. 28, 1988; pp. 345-348.
Hornykiewicz, Oleh; "Biochemical aspects of Parkinson's disease"; Neurology; 51; 1998; pp. S2-S9.
Kish, Stephen J. et al.; "Uneven Pattern of Dopamine Loss in the Striatum of Patients with Idiopathic Parkinson's Disease"; Pathophysiologic and Clinical Implications; The New England Journal of Medicine; vol. 318; No. 4; Apr. 7, 1988; pp. 876-880.
Misko, Albert et al.; "Mitofusin 2 Is Necessary for Transport of Axonal Mitochondria and Interacts with the Miro/Milton Complex"; Neurobiology of Disease; The Journal of Neuroscience; 30(12); pp. 4232-4240.
Pham, Anh H. et al.; "Mouse lines with photo-activatable mitochondria (PhAM) to study mitochondrial dynamics"; Genesis; Nov. 2012; 50(11); pp. 833-843.
Pifl, Ch. et al.; "Effect of 1-Methyl-4-Phenyl-1,2,3,6-Tetrahydropyridine on the Regional Distribution of Brain Monoamines in the Rhesus Monkey"; Neuroscience; vol. 44; No. 3; 1991; pp. 591-605.
Stoessl, A. Jon; "Neuroimaging in Parkinson's Disease"; Neurotherapeutics : The journal of the American Society for Experimental NeuroTherapeutics; vol. 8; Jan. 2011; pp. 72-81.

* cited by examiner

*Primary Examiner* — Titilayo Moloye
(74) *Attorney, Agent, or Firm* — Lewis Roca Rothgerber Christie LLP

(57) ABSTRACT

An animal model for Parkinson's disease has a disrupted Mfn2 gene in dopaminergic neurons. The Mfn2 gene disruption results in severe movement disorder attributed to progressive degeneration of the nigrostriatal circuit as found in Parkinson's disease. The animal model having exogenous suppression of the Mfn2 gene in dopaminergic neurons is a suitable animal model for studying Parkinson's disease.

5 Claims, 18 Drawing Sheets
(9 of 18 Drawing Sheet(s) Filed in Color)

FIG2A
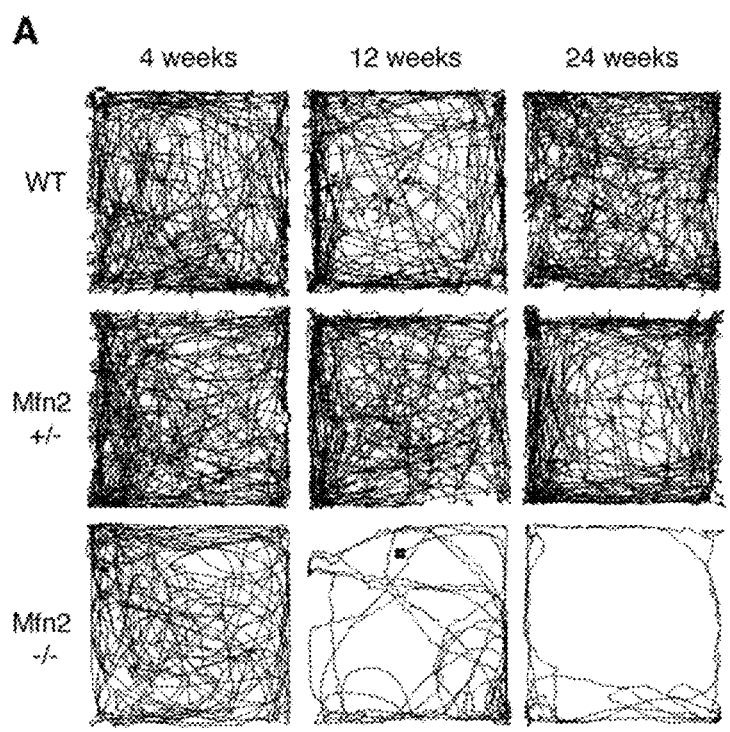
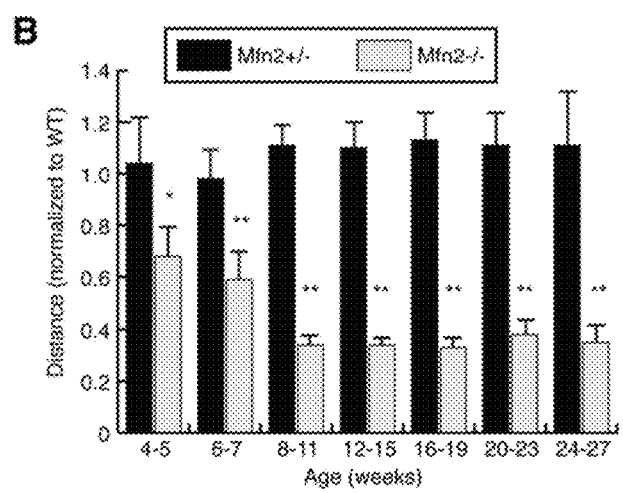
FIG2B

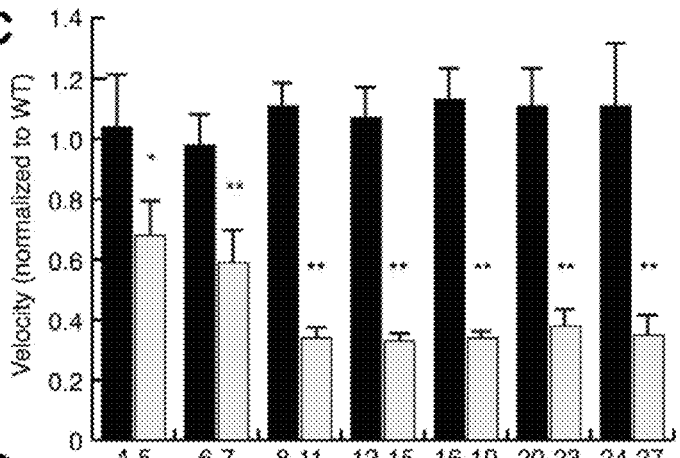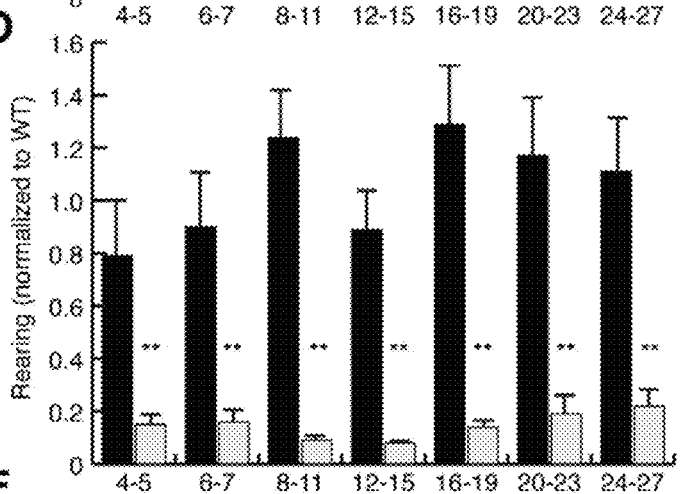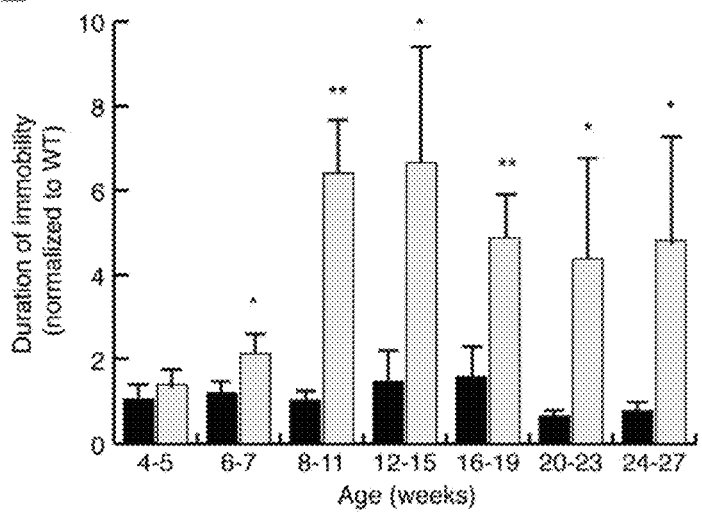

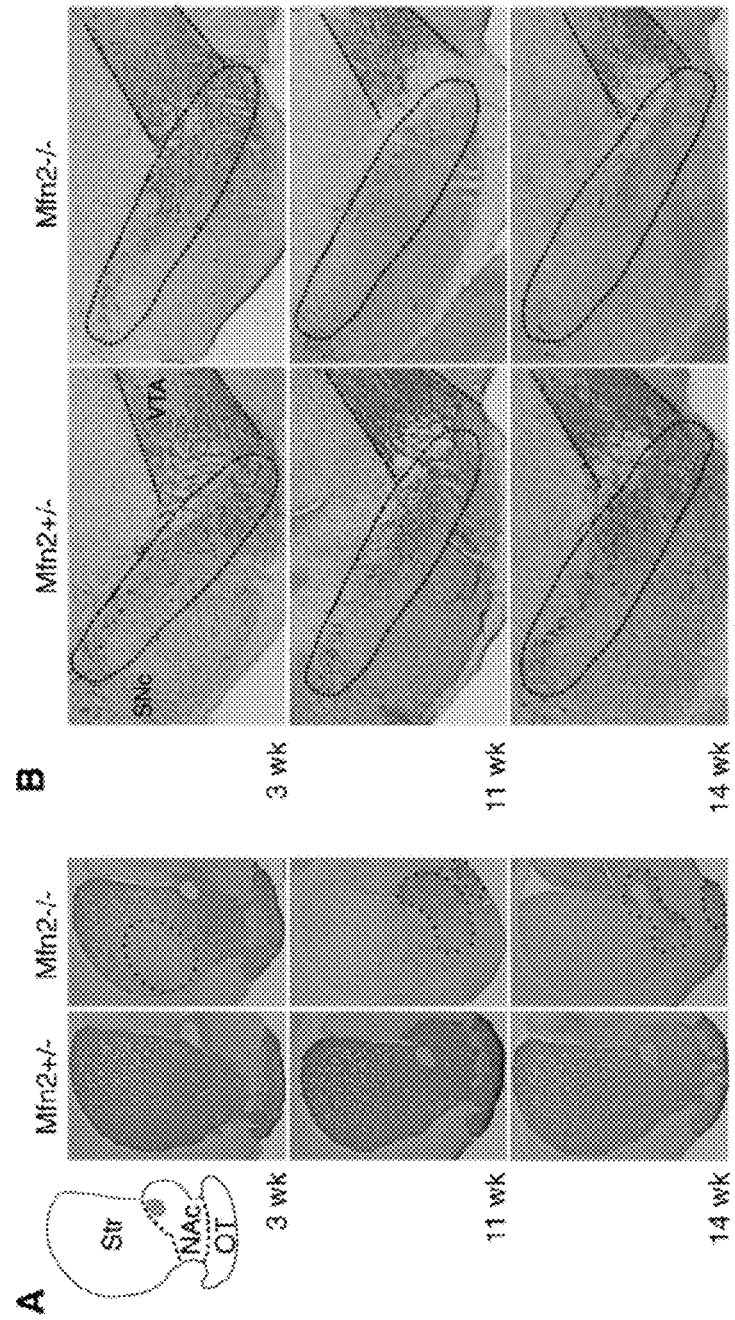

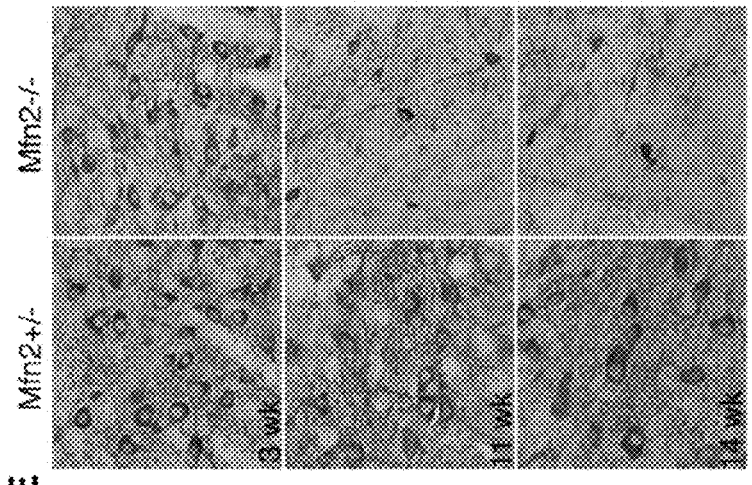
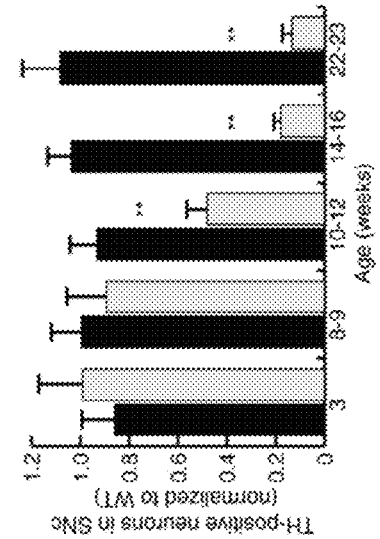
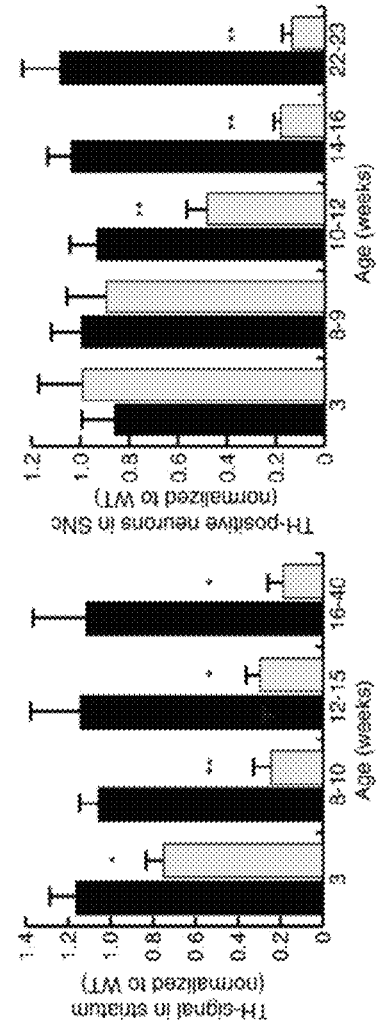
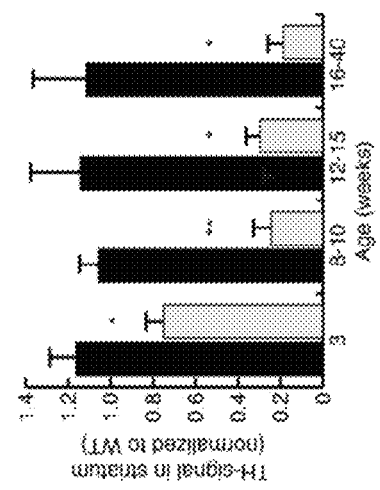

20 um

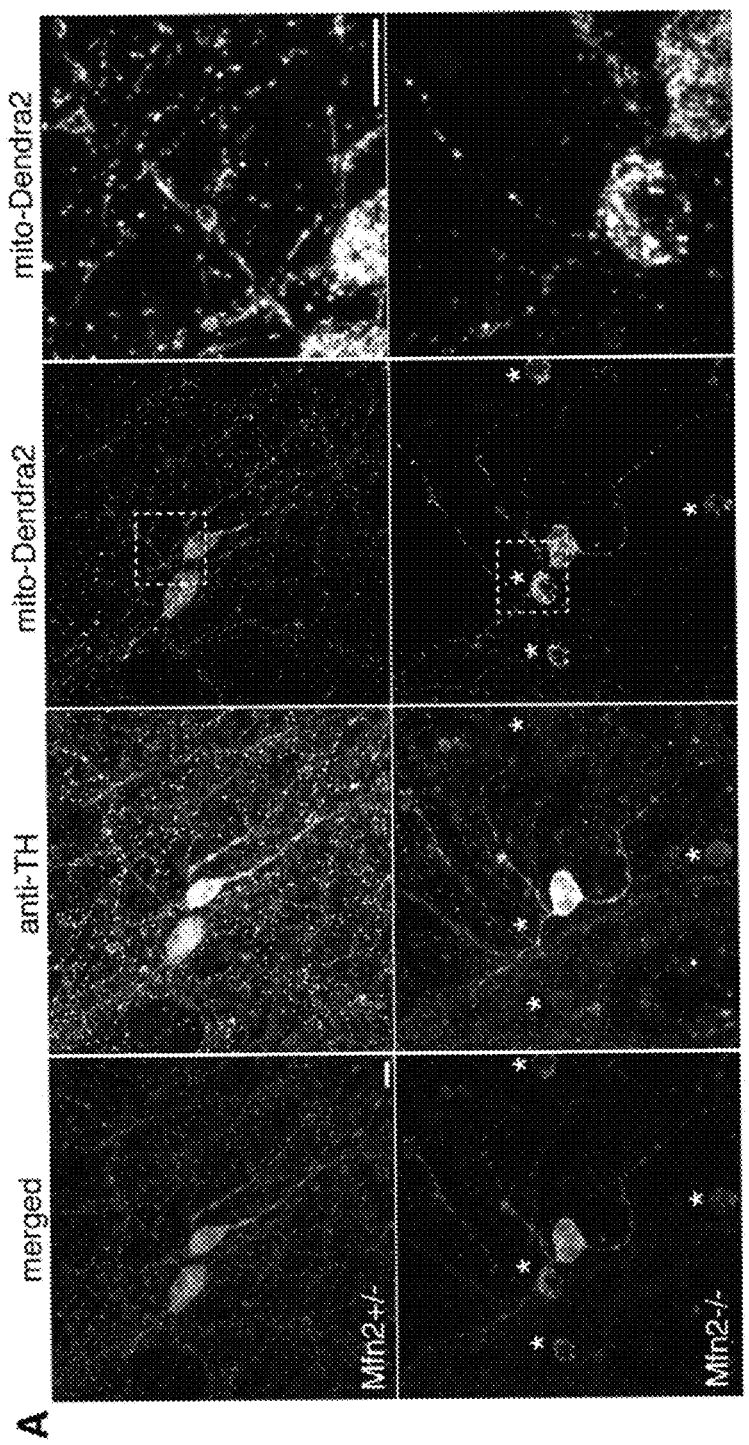

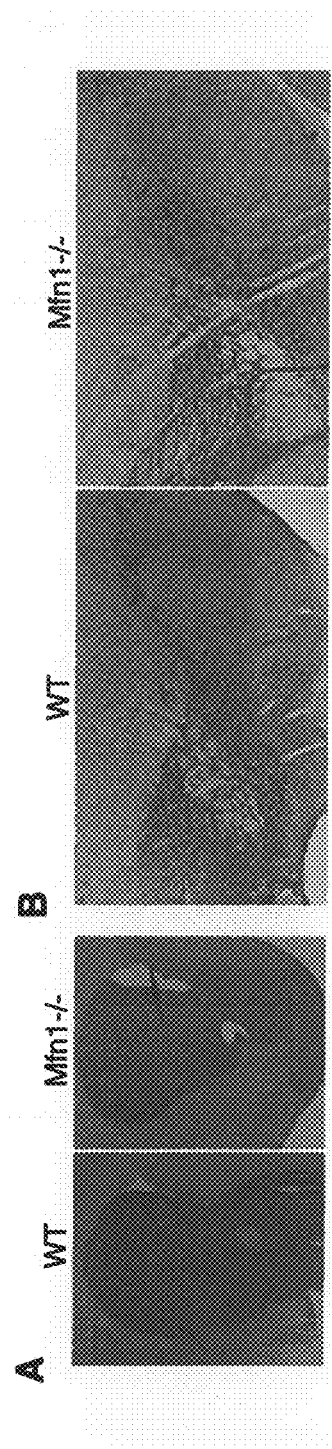

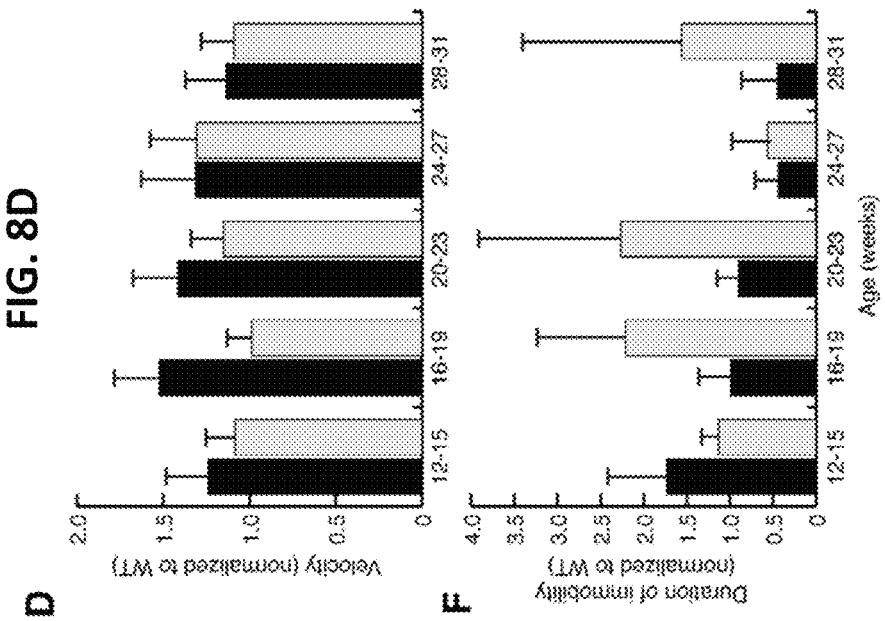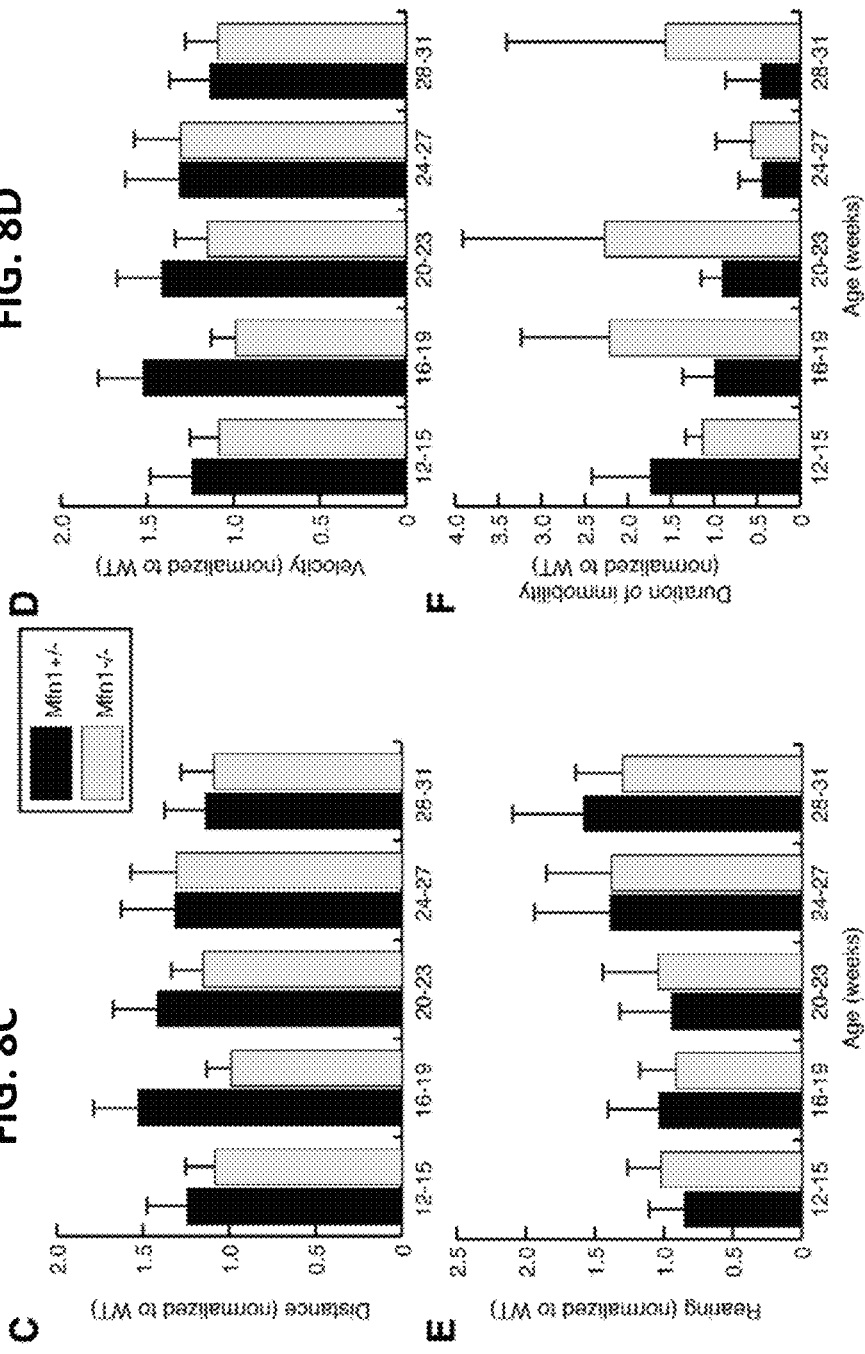

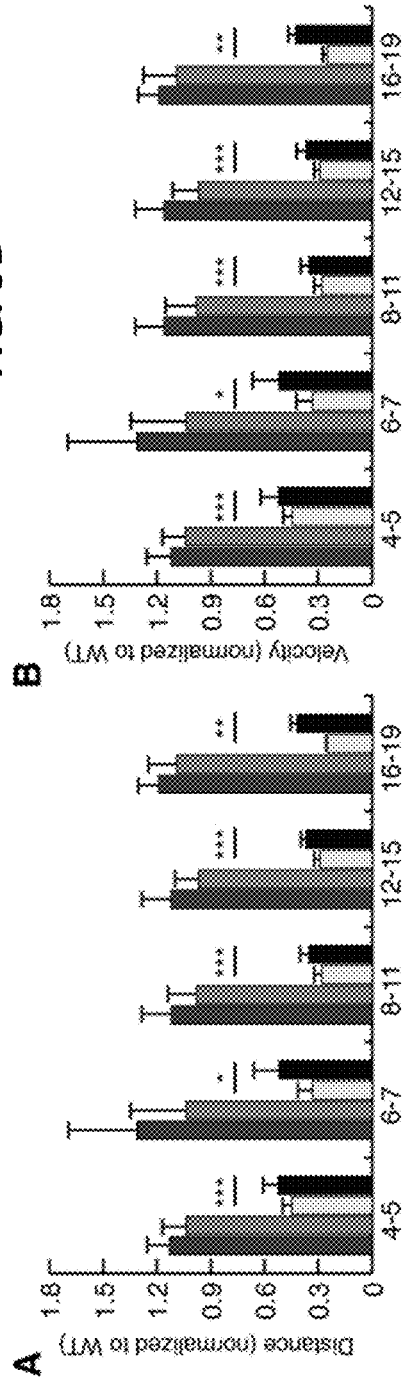
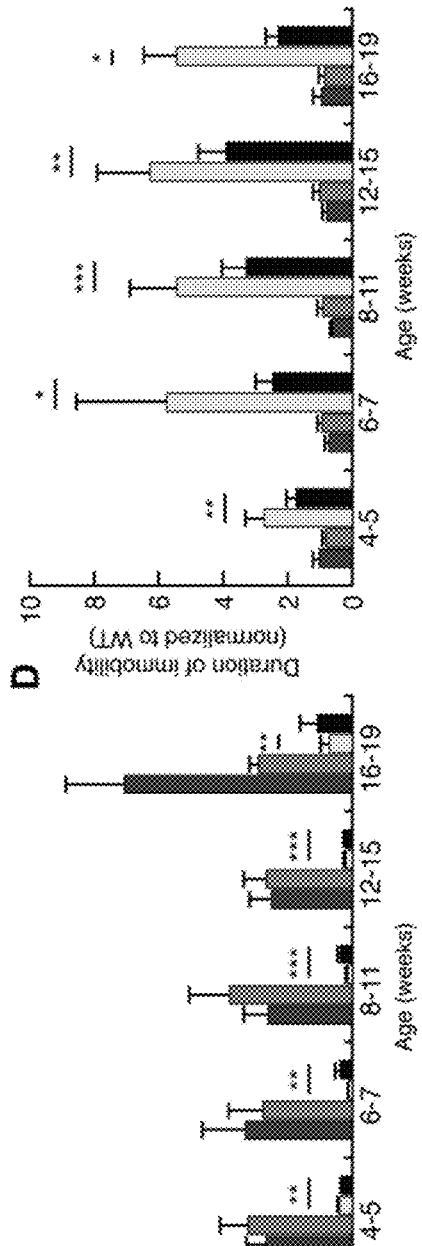
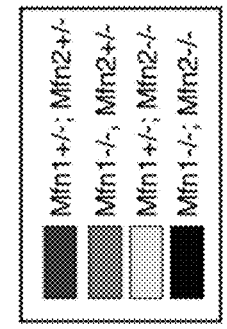
FIG. 9A
FIG. 9B
FIG. 9C
FIG. 9D

TRANSGENIC MOUSE HAVING A GENOME COMPRISING A HOMOZYGOUS DISRUPTION OF THE ENDOGENOUS MFN2 GENE EXPRESSION IN THE DOPAMINERGIC NEURONS

CROSS-REFERENCE TO RELATED APPLICATION(S)

The present application claims priority to and the benefit of U.S. Provisional Application Ser. No. 61/662,523 filed on Jun. 21, 2012, the entire contents of which are incorporated herein by reference.

STATEMENT REGARDING FEDERALLY SPONSORED RESEARCH OR DEVELOPMENT

This invention was made with government support under R01 GM062967 awarded by the National Institutes of Health. The government has certain rights in the invention.

FIELD

This disclosure is directed to an animal model for Parkinson's disease.

BACKGROUND

Parkinson's disease (PD) is a neurodegenerative movement disorder characterized by resting tremor, rigidity, bradykinesia, and postural instability. PD symptoms are classically attributed to dopamine depletion and the degeneration of dopaminergic neurons in the substantia nigra pars compacta (SNc). However, additional neuronal circuits are affected, and non-motor symptoms are often present, suggesting a systemic pathology. There is compelling evidence that mitochondrial dysfunction is a primary event in the disease process.

It has been reported that PD-related mutations and mitochondrial dynamics have a reciprocal relationship. PD-related mutations can perturb mitochondrial dynamics, and the consequences of these mutations can be modulated by mitochondrial dynamics. As such, there is a need to understand the function of mitochondrial dynamics in dopaminergic neurons to better understand Parkinson's disease.

SUMMARY

In some embodiments, an animal model having characteristics of Parkinson's disease has exogenous suppression of the Mfn2 gene in dopaminergic neurons of the animal model. In some embodiments, exogenous suppression of the Mfn2 gene includes a nucleic acid sequence inserted within the Mfn2 gene locus. In some embodiments, the nucleic acid sequence encodes for a photo-activatable fluorescent protein that is capable of targeting mitochondria.

In some embodiments, the animal model has suppressed Mfn2 expression in substantia nigra cell groups, for example, the A8, A9 and A10 cell groups.

In some embodiments of the present invention, the animal model is a mouse model.

In some embodiments of the present invention, a method of studying Parkinson's disease, including studying the animal model having exogenous suppression of the Mfn2 gene in dopaminergic neurons.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 2A shows representative traces from open field analysis, where the traces represent spontaneous movement in an open field during a 15-minute observation period; the genotypes and ages of the mice are indicated, according to embodiments of the present invention.

FIG. 2B shows the distanced traversed by the indicated mouse in the open field, according to embodiments of the present invention.

FIG. 2C shows the average velocity by the indicated mouse in the open field, according to embodiments of the present invention.

FIG. 2D shows the rearing frequency by the indicated mouse in the open field, according to embodiments of the present invention.

FIG. 2E shows the immobile periods between activity by the indicated mouse in the open field, according to embodiments of the present invention.

FIG. 3A. shows dopaminergic projections to the striatum (Str), nucleus accumbens (NAc), and olfactory tubercle (OT), in which the diagram delineates these regions, the sections were stained with TH antibody to label dopaminergic projections (brown pigment); at 3 weeks of age, Mfn2 mutant animals show decreased TH-immunoreactive terminals in the dorsolateral striatum (outlined region); later time points reveal widespread loss in the striatum; and VTA projections to the Ac and OT are still present at 11 and 14 weeks (outlined regions in bottom 2 panels), according to embodiments of the present invention.

FIG. 3B shows dopaminergic neurons at the SNc and VTA, in which sections of the midbrain were stained with TH and counterstained with Cresyl violet (blue) to identify dopaminergic neurons, where at 11 and 14 weeks, the Mfn2 mutants exhibit reduced staining in the SNc, whereas the VTA is relatively preserved. The SNc and VTA regions are outlined, according to embodiments of the present invention.

FIG. 3C shows quantification of TH-staining, in which measured values of TH-positive signal from heterozygous and homozygous animals were normalized to wildtype controls, where for each animal, 3 sections were measured, and the Student t-test was used to obtain p-values (* $p<0.05$; ** $p<0.001$; n=3-6), and error bars represent propagated error, according to embodiments of the present invention.

FIG. 3D shows quantitation of dopaminergic cell loss in the SNc, in which counts from heterozygous and homozygous animals were normalized to wildtype controls (n=2 for 8-9 week, n=3 for remainder), and for each animal, 9 sections spanning the rostro-caudal extent of the midbrain were manually counted, with statistical analysis performed as in FIG. 3C, according to embodiments of the present invention.

FIG. 3E shows magnified images of FIG. 3B showing loss of dopaminergic neurons and processes in Mfn2 mutant animals, according to embodiments of the present invention.

FIGS. 5A-5C show mitochondrial fragmentation and depletion in slice cultures of Mfn2 mutants with cre-mediated expression of mito-Dendra2 labeling the dopaminergic neurons.

FIG. 5A shows slice cultures of heterozygous controls and Mfn2 mutants, in which the slices were immunostained with TH (red); the first column shows a merged image of TH and mito-Dendra2 fluorescence (green) while the last column is an enlargement of the boxed zone, and the asterisks highlight degenerating Mfn2-null neurons that have diminished or absent TH staining, according to embodiments of the present invention.

FIG. 5B shows mito-Dendra2 signal in neuronal projections, where depletion of mitochondria in both proximal and distal processes is evident in Mfn2 mutant slices, according to embodiments of the present invention.

FIG. 5C shows quantification of mitochondrial mass normalized to the number of dopaminergic neurons, where for each sample, the total mito-Dendra2-positive area in a 5 mm×5 mm region was measured and normalized to the number of Dendra2-positive neurons; the mitochondrial mass is reported as percentage area of heterozygous control±SEM; the Student t-test was used to evaluate statistical significance (* $p<0.001$; n=5 for mutant slices; n=7 for control), and the scale bar represents 10 µm for all images, according to embodiments of the present invention.

FIG. 8A shows representative images of TH-immunoreactivity in striatum of Mfn-1-null mice at 22 weeks of age, where no loss is evident, according to embodiments of the present invention.

FIG. 8B shows representative images of TH-immunoreactivity in the midbrain of Mfn-1-null mice at 22 weeks of age, where no loss is evident, according to embodiments of the present invention.

FIG. 8C shows the total distance traveled for indicated Mfn1 mutants, in which results of heterozygous and homozygous mutants were normalized to wildtype controls, and error bars represent propagated standard error, according to embodiments of the present invention.

FIG. 8D shows the average velocity for indicated Mfn1 mutants, in which results of heterozygous and homozygous mutants were normalized to wildtype controls, and error bars represent propagated standard error, according to embodiments of the present invention.

FIG. 8E shows the rearing frequency for indicated Mfn1 mutants, in which results of heterozygous and homozygous mutants were normalized to wildtype controls, and error bars represent propagated standard error, according to embodiments of the present invention.

FIG. 8F shows the immobile duration for indicated Mfn1 mutants, in which results of heterozygous and homozygous mutants were normalized to wildtype controls, and error bars represent propagated standard error, according to embodiments of the present invention.

FIG. 9A shows the total distance traveled over 15 minutes in Mfn-double mutants, where for all calculations, values are normalized to wildtype controls and error bars indicate the propagation of standard error, and the Student t-test was used to calculate statistical significance (n=3-9 animals), * $p<0.05$;  p,0.01; * $p<0.001$, according to embodiments of the present invention.

FIG. 9B shows the average velocity exhibited by indicated Mfn-double mutants, where for all calculations, values are normalized to wildtype controls and error bars indicate the propagation of standard error, and the Student t-test was used to calculate statistical significance (n=3-9 animals), * $p<0.05$;  p,0.01; * $p<0.001$, according to embodiments of the present invention.

FIG. 9C shows the rearing frequency exhibited by indicated Mfn-double mutants, where for all calculations, values are normalized to wildtype controls and error bars indicate the propagation of standard error, and the Student t-test was used to calculate statistical significance (n=3-9 animals), * p<0.05;  p,0.01; *p<0.001, according to embodiments of the present invention.

FIG. 9D shows the average duration of immobility between bouts of activity exhibited by indicated Mfn-double mutants, where for all calculations, values are normalized to wildtype controls, and error bars indicate the propagation of standard error, and the Student t-test was used to calculate statistical significance (n=3-9 animals), * p<0.05;  p<0.01; *p<0.001, according to embodiments of the present invention.

DETAILED DESCRIPTION

Figure 1A:
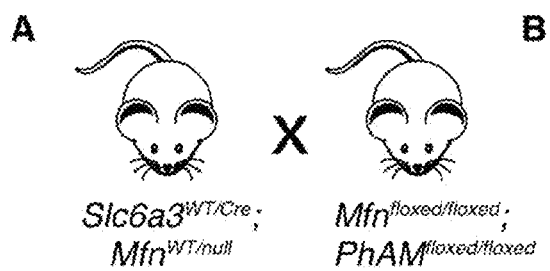
FIG. 1A is a mating scheme in which Slc6a3-Cre is controlled by the dopamine transporter locus and is expressed in a subset of dopaminergic neurons, particularly the SNc, VTA, and retrorubral field (RRF), in which the cross also incorporates a cre-induced, mitochondrially targeted Dendra2 (termed PhAM), according to embodiments of the present invention.

Embodiments of the present invention disclose an animal model having the hallmark characteristics of Parkinson's disease. These characteristics include resting tremor, rigidity, bradykinesia, and postural instability. As disclosed herein, an animal model having the Mfn2 gene disrupted displays a Parkinson's phenotype as described in the examples and figures herein. This Mfn2 gene knock-out (KO) was performed in a mouse in which the Mfn2 gene was disrupted in substantia nigra (SN) cell groups. This targeted MFn2 gene disruption was specifically targeted in these SN cell groups using a Slc6a3-Cre expression system, as described herein.

As used herein, exogenous suppression refers to the inhibition of gene expression. For example, the exogenous suppression of the Mfn2 gene may include a genetic disruption such as insertion, substitution, and/or deletion within the Mfn2 gene locus. It is understood by those of ordinary skill in the art that a genetic disruption may not delete the entire gene, but inhibits expression of the gene. Furthermore, the gene disruption could also include upstream regulation wherein the gene is present, but the expression of the gene is suppressed.

In some embodiments, exogenous suppression of the Mfn2 gene includes targeting a knock-out sequence to the Mfn2 gene locus in dopaminergic neurons using a recombinase expression system that specifically targets dopaminergic neurons. A knock-out sequence is any nucleic acid sequence that is capable of inserting (e.g., recombining) at selected sites around or within the gene sequence. For example, the Slc6a3-Cre expression system allows for gene targeting specifically in the substantia nigra cell groups.

In some embodiments, an animal model has a nucleic acid sequence encoding for a mitochondrially-targeted photo-activatable fluorescent protein (PAFP) that recombines at the Mfn2 gene locus of dopaminergic neurons. A mito-PAFP labels the mitochondria thereby enabling the monitoring of the mitochondria in isolated cells or in the whole animal model.

The studying of Parkinson's disease using the disclosed animal model includes observing effects of potential drug compounds on any of the characterized traits including movement tests, histological analysis, and molecular characterization of the cellular processes. Examples of suitable assays are known in the art, examples of which are disclosed herein.

As disclosed herein, the loss of Mfn2 results in a severe movement disorder attributed to progressive degeneration of the nigrostriatal circuit as found in Parkinson's disease. Accordingly, in embodiments of the present invention, the animal model having exogenous suppression of the Mfn2 gene in dopaminergic neurons is a suitable animal model for studying Parkinson's disease.

The following Examples are presented for illustrative purposes only, and do not limit the scope or content of the present application.

EXAMPLES

Reference is made to U.S. patent application Ser. No. 13/923,218, titled "Animal Model Having Photo-Activatable Mitochondria," filed Jun. 20, 2013, and Pham et al, 2012, *Genesis*, 50:833-843, the entire contents of both of which are incorporated herein by reference.

Example 1

Deletion of Mfn2 from Dopaminergic Neurons

Figure 1B:
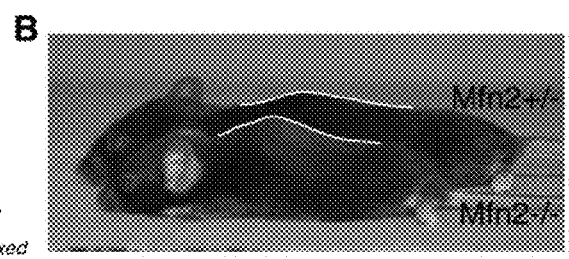
FIG. 1B is a representative image of a 22 week old Mfn2 mutant knock-out mouse compared to a heterozygous littermate (Het), showing the small size and severe kyphosis of the Mfn2 mutant mice, according to embodiments of the present invention.
Figure 1C:
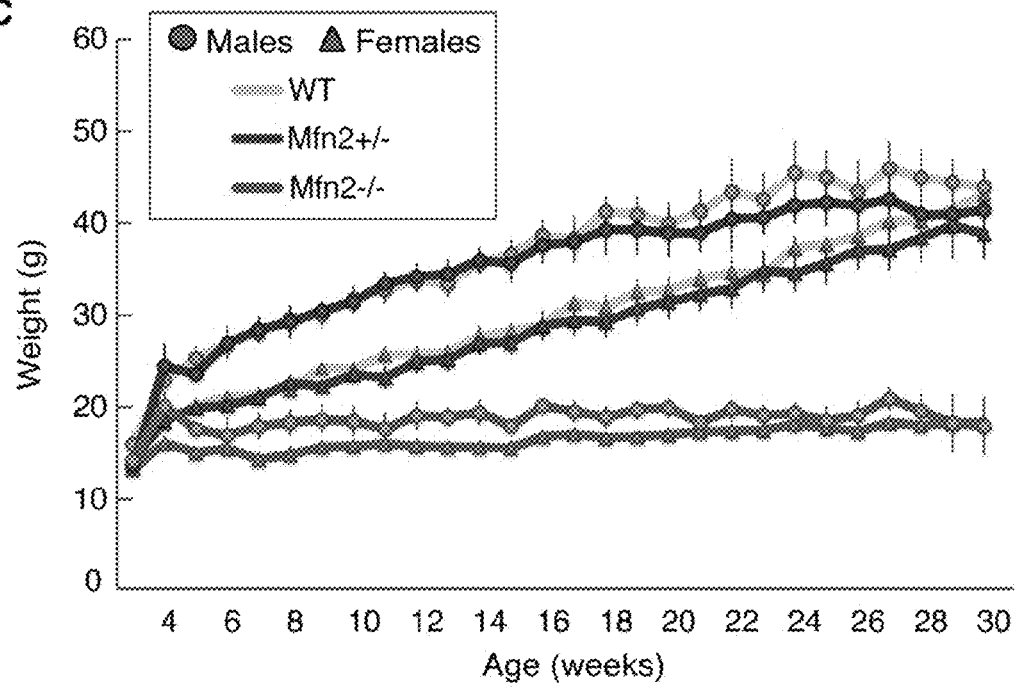
FIG. 1C is a plot of weekly weight measurements, in which each point represents the average weight±SEM (n=10-15 for each genotype and sex), and both male and female Mfn2 mutants are significantly smaller ($p<0.05$, two-tailed Student t-test) than control animals at 5 weeks of age, according to embodiments of the present invention.

A genetic approach was used to assess the role of mitochondrial fusion in dopaminergic neurons. Mfn1 and Mfn2 conditional knockout mice were crossed to the Slc6a3-Cre driver (Backman, C. M., et al, 2006, *Genesis*, 44, 383-390, the entire contents of which are herein incorporated by reference), in which the endogenous dopamine transporter locus expresses Cre recombinase in the A8-A10 subset of dopaminergic neurons, including those of the SNc (FIG. 1A). The mating scheme also incorporated a mito-Dendra2 Cre reporter for the dual purpose of labeling mitochondria and monitoring Cre-dependent excision. Mice with disruption of Mfn1 show no phenotype up to 1 year of age (FIGS. 8A-8F). In contrast, mice with disruption of Mfn2 are hunched and hypoactive by 5 weeks of age when compared to wildtype or heterozygous Mfn2 littermates. These mice also exhibit kyphosis and reduced activity (FIG. 1B). Weight gain is stagnant after 4 weeks of age, resulting in an increasingly larger weight difference between mutant and control littermates (FIG. 1C).

In an initial cohort of Mfn2 mutants, many animals died at approximately 6-7 weeks of age due to apparent malnutrition. Mutant animals (n=15) died or were culled due to significant weight loss between 36 and 48 days of age. However, when supplied with hydrated gel packs and crushed pieces of regular chow on the cage floor, all mutant Mfn2 mice survive beyond 6 months, with a majority surviving past 1 year of age. It is believed that these mice have difficulty accessing food and water in normal cages due to a severe rearing defect. In this respect, the disclosed mice are distinct from other dopamine depletion models that exhibit aphagia and adipsia even when food is placed nearby. To minimize possible secondary effects due to malnutrition, the phenotypic analyses reported below were performed using mutant and control mice provided with this dietary supplementation.

Example 2

Movement Disorder in Mfn2 Mutants

Because initial observations suggested that Mfn2 mutant mice had reduced activity, the spontaneous movements were monitored in a longitudinal open field study. Mfn2 mutant mice show an age-dependent decline in locomotive activity (FIG. 2A). At 4-5 weeks, mutant animals travel only 68% of the distance traversed by wildtype control animals. This defect progresses over the next several weeks. By 8-11 weeks of age, the distance traveled by mutants reduces to 34% of wildtype controls (FIG. 2B). In contrast, Mfn2 heterozygous animals show normal locomotion. The Mfn2 homozygotes were compared to both wildtype controls and heterozygous controls carrying Slc6a3-Cre, because the knock-in Cre allele causes a slight, non-significant, decrease in dopamine transporter levels in the heterozygous state. It was found that Mfn2 heterozygotes carrying Slc6a3-Cre are indistinguishable from wildtype controls in all the assays used in this study.

Similar to travel distance, the speed of movement exhibited by Mfn2 mutant mice declines with age (FIG. 2C). A strong rearing defect in mutant Mfn2 mice that is present as early as 4 weeks of age was also observed (FIG. 2D). This postural defect likely contributes to the starvation and dehydration observed at 6 weeks when cages are not supplemented with food and gel packs on the floor. Consistent with the decreased locomotion, Mfn2 mutants spend twice as much time inactive at 6-7 weeks of age. By 8-11 weeks, this discrepancy increases to 6-fold (FIG. 2E). Of note, the locomotive defect is specific for Mfn2 mutants; Mfn1 mutants show no motor deficiency in the open field test (FIGS. 8A-8F). Moreover, the double Mfn1/Mfn2 mutants do not have an exacerbated phenotype compared to Mfn2 mutants (FIGS. 9A-9D). Overall, measurements from the open field test suggest that, beginning at 4-5 weeks, Mfn2 mutants exhibit progressive bradykinesia and a postural defect, both cardinal signs of PD.

For the measurements in FIGS. 2A-2E, values from the heterozygous and homozygous animals were normalized to that of the wildtype controls, and error bars represent propagated standard error. The Student t-test was used to obtain p-values between Mfn2 mutants and wildtype controls (* $p<0.05$; ** $p<0.001$; $n=6-10$ animals per age and genotype).

Example 3

Retrograde Degeneration of SNc Dopaminergic Neurons

To determine whether the motor deficits in mutant animals are accompanied by a loss of dopaminergic innervation, tyrosine hydroxylase (TH)-immunoreactivity was used to assess the nigrostriatal circuit. The striatum was analyzed first, the endpoint of the nigrostriatal pathway. Here, TH-staining marks the axon terminals derived from the SNc. In Mfn2 mutants, the striatum shows a 25% reduction in dopaminergic terminals at 3 weeks of age (FIGS. 3A, 3C). Loss of TH-immunoreactivity is detected first in the dorsolateral striatum (FIG. 3A, outlined region in 3 week sample) and gradually encompasses the entire striatum by 11 weeks. Interestingly, the regional severity of striatal loss in Mfn2 mutants resembles the pattern described in PD patients, as described in Kish, S. J. et al, 1988, *The New England Journal of Medicine*, 318, 876-880, and Stoessl, A. J., 2011, *Neurotherapeutics: The journal of the American Society for Experimental NeuroTherapeutics*, 8, 72-81, the entire contents of both of which are herein incorporated by reference.

By 8-10 weeks, the depletion of dopaminergic terminals increases to 76% in Mfn2 mutant animals (FIG. 3C). In contrast, the projections to the nucleus accumbens (NAc) and olfactory tubercle (OT), which come from dopaminergic neurons in the ventral tegmental area (VTA), appear to be more protected. These dopaminergic terminals, which are part of the mesolimbic pathway, are moderately preserved at 11-14 weeks (FIG. 3A, outlined regions).

Moving upstream in the nigrostriatal circuit, the number of TH-immunoreactive neurons was counted in the SNc. In contrast to the striatum, there is no notable loss of TH-positive neurons in the SNc at either 3 weeks or 8-9 weeks (FIGS. 3B, 3D). The earliest time point with neuronal loss occurs at 10-12 weeks, with a 52% decrease in TH-immunopositive neurons. Further degeneration followed at subsequent ages (FIG. 3D). Additionally, the neurons remaining in Mfn2 mutants appear to have smaller cell bodies as well as diminished neuronal processes (FIG. 3E). Partial loss of neurons was also observed at the VTA but not to the extent of the SNc.

Figure 4A:
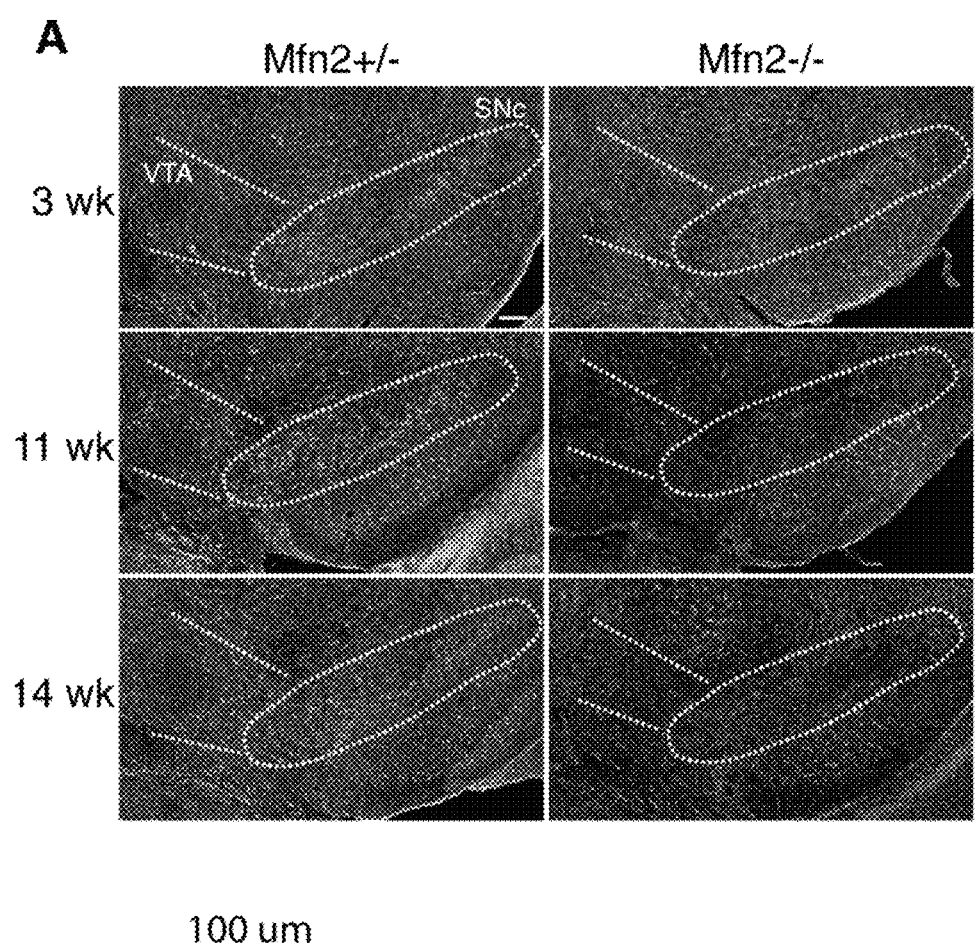
FIG. 4A shows a loss of dopaminergic neurons in the SNc, where the coronal midbrain slices were analyzed by fluorescent Niss1 staining to highlight neurons, with the SNc indicated by the outlined oval, and a reduction in neurons in the SNc is apparent by 11 weeks in the Mfn2-null mutant, with the scale bar representing 100 µm, according to embodiments of the present invention.
Figure 4B:
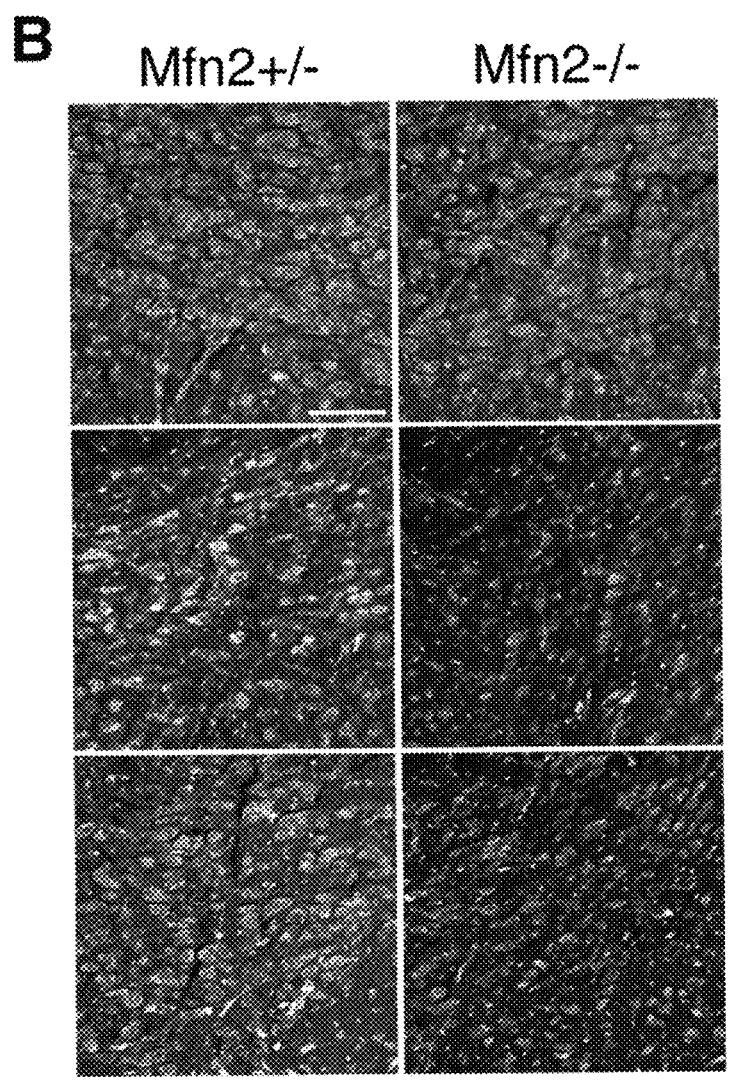
FIG. 4B shows high magnification images of Niss1-stained cells in the SNc, with the scale bar representing 20 µm, according to embodiments of the present invention.

Because degenerating neurons can lose expression of neuronal markers, loss of TH immunoreactivity does not necessarily indicate neuronal loss. To directly evaluate the loss of neurons, Nissl staining of the SNc (FIGS. 4A-4C) was performed. Normal staining was observed at 3 weeks of age, but by 11 weeks and beyond, the SNc showed a reduced density of Nissl-stained cells. Taken together, these results indicate two pertinent features of neurodegeneration in this mouse model. First, multiple types of dopaminergic neurons have a requirement for Mfn2, but the nigrostriatal circuit exhibits enhanced vulnerability compared to the mesolimbic pathway. Likewise, SNc neurons in PD patients are more severely affected than the VTA population, as disclosed in Hirsch, E. et al, 1988, *Nature*, 334, 345-348, and Damier, P. et al., 1999, *Brain: A Journal of neurology*, 122 (Pt 8), 1437-1448, the entire contents of both of which are herein incorporated by reference.

Second, the degeneration of Mfn2-deficient dopaminergic neurons occurs in a stepwise manner. The initial defects appear at the axon terminals, followed one to two months later by degeneration of the cell bodies.

Example 4

Mitochondrial Fragmentation and Depletion in Dopaminergic Neurons

A Cre reporter of mitochondrial dynamics that targets the photo-convertible fluorescent protein Dendra2 to the mitochondrial matrix (Pham et al., 2012 supra). The expression of mito-Dendra2 relies on Cre-mediated excision of an upstream loxP-flanked termination signal. In the mating scheme of FIG. 1A, mito-Dendra2 expression depends on the Slc6a3-Cre driver, thereby allowing us to visualize mitochondria within the affected neurons, a key benefit in the densely populated midbrain. A slice culture system was established to assess mitochondrial dynamics in Mfn2-null dopaminergic neurons. The organotypic culture system has been extensively used for long-term assessment of neuronal function and development in vitro, because it preserves the cytoarchitecture and circuitry between multiple brain regions. To best preserve the nigrostriatal connections, the brains were sectioned at an angle previously characterized to retain these projections as described in Ammari, R et al., 2009, *Neuroscience*, 159, 3-6, and Beurrier, C. et al., 2006, *Neuroscience*, 140, 77-86, the entire contents of both of which are herein incorporated by reference.

Figure 5B:
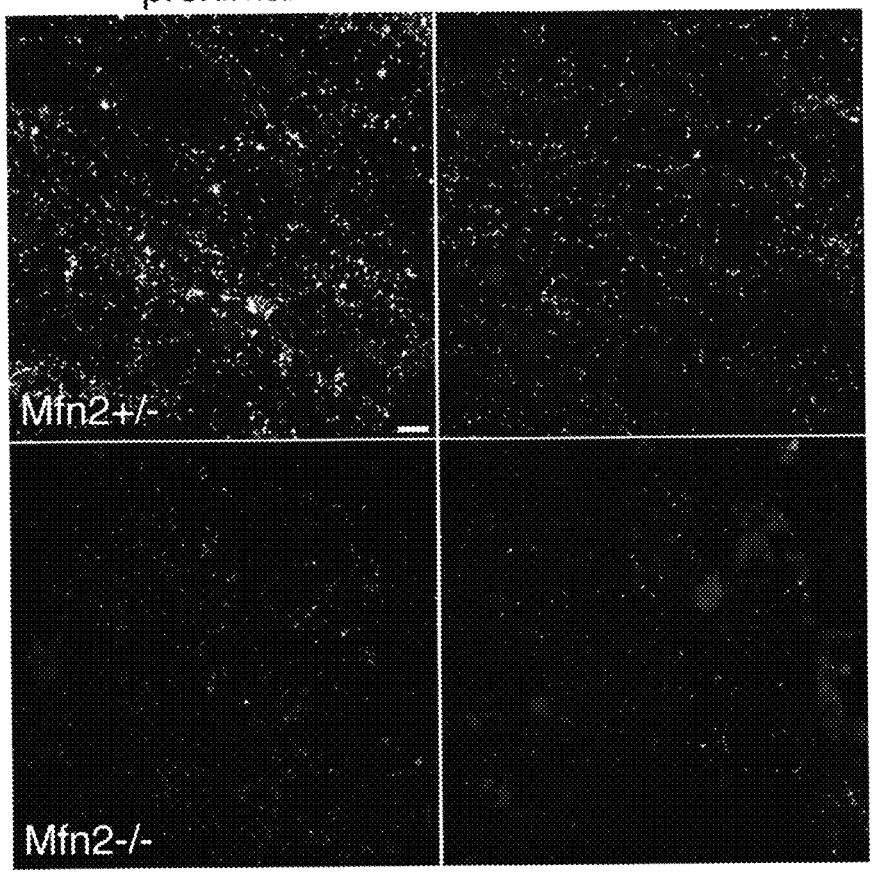
Figure 5C:
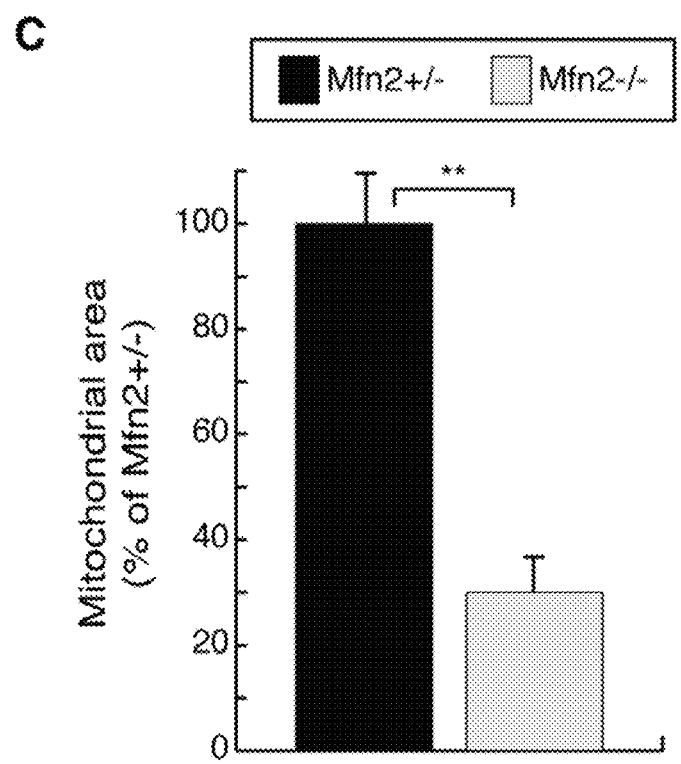

In slice cultures from wildtype and heterozygous brains, it was found that Slc6a3-Cre/mito-Dendra2 expression is specific for dopaminergic neurons, as evidenced by its restriction to cells with TH immunoreactivity (FIG. 5A). The mitochondria in control heterozygous slices have a mixed morphology profile, consisting of both tubular structures in proximal processes and short puncta in distal projections. In Mfn2-null slices, swollen and fragmented mitochondria were found in the soma and proximal processes. Consistent with the histological analysis (FIG. 3E), the Mfn2 mutant neurons have fewer and thinner processes extending from the cell body (FIG. 5A). In addition, the Mfn2 mutant cultures contain many neurons that express mito-Dendra2 but lack or have reduced TH signal. The failure to maintain TH expression suggests that these neurons are at an intermediate stage of degeneration (FIG. 5A, starred neurons). It is also noted that there is a severe depletion of mitochondria in neuronal processes both proximal and distal to dopaminergic cell bodies (FIG. 5B). Mutant slices show a 70% reduction in mitochondrial mass after normalizing to mito-Dendra2-positive cell bodies (FIG. 5C).

Example 5

Decreased Mitochondrial Transport Along Nerve Processes in Mfn2 Mutants

Figure 6A:
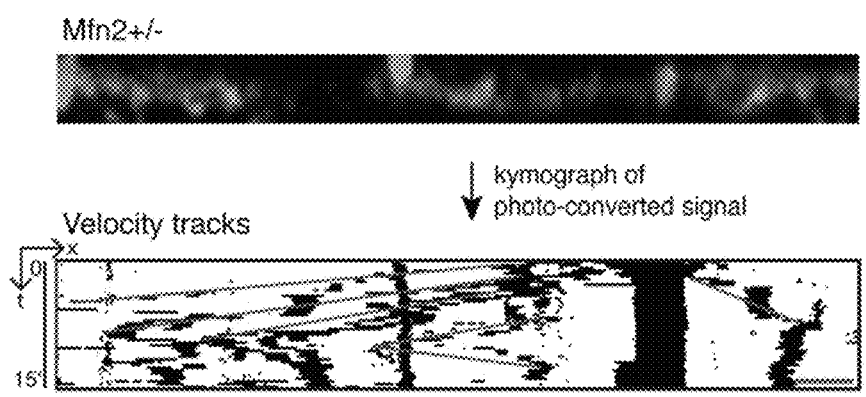
FIG. 6A. shows a representative mitochondrial transport tracking experiment of an Mfn2 heterozygous control, in which a subset of mitochondria in the nerve process was photo-converted to red for time-lapse imaging, and the images of the photo-converted signal were processed into a kymograph to visualize mitochondrial movement (binary image); the velocity measurements were calculated from the red tracks that overlay mitochondrial trajectories, according to embodiments of the present invention.
Figure 6B:
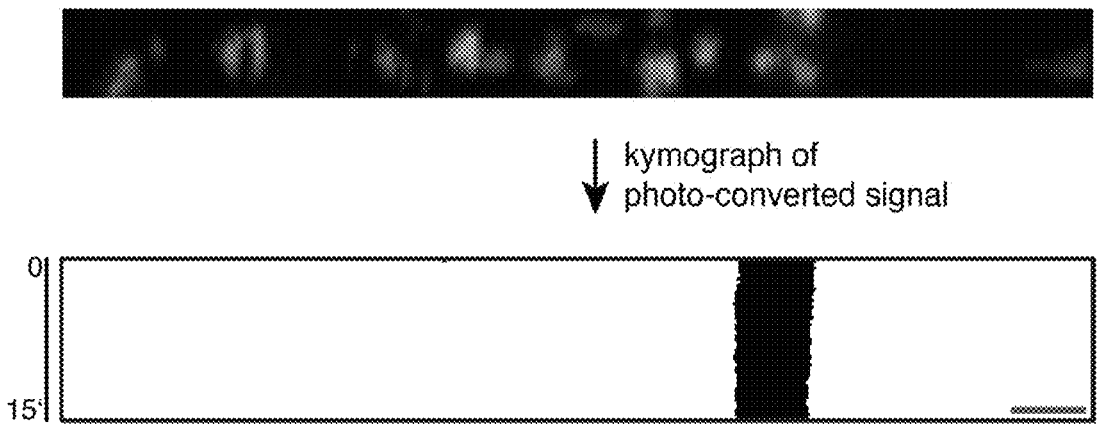
FIG. 6B shows a representative tracking experiment in an Mfn2 mutant showing loss of mitochondrial transport, according to embodiments of the present invention.
Figure 6C:
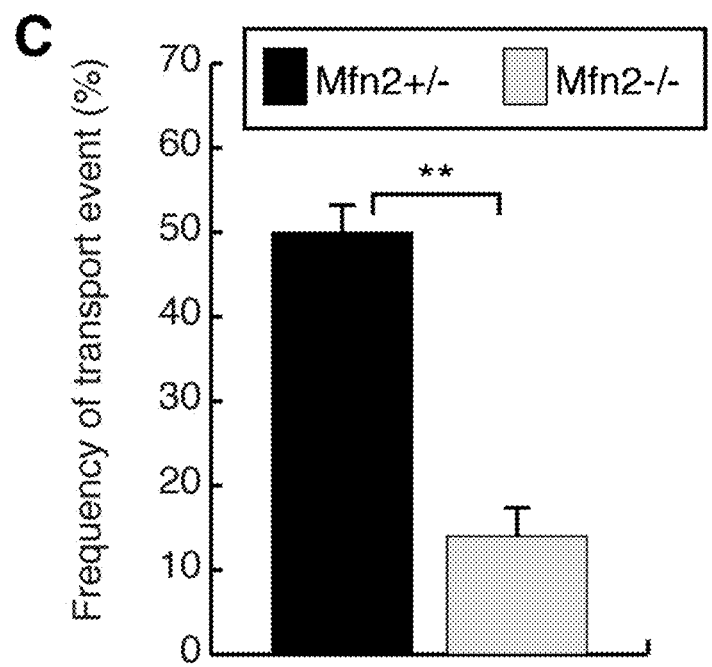
FIG. 6C shows quantification of mitochondrial transport in neuronal processes, in where for each photo-conversion experiment, a positive event was defined as directed movement of more than 5 µm during the 15 minute recording session; the graph shows the frequency of photo-conversion experiments that resulted in at least one positive event, and for Mfn2 heterozygous slices, 150 experiments were scored; for Mfn2 mutant slices, 138 experiments were scored; the Student t-test was used to calculate statistical significance (** $p<0.001$), according to embodiments of the present invention.
Figure 6D:
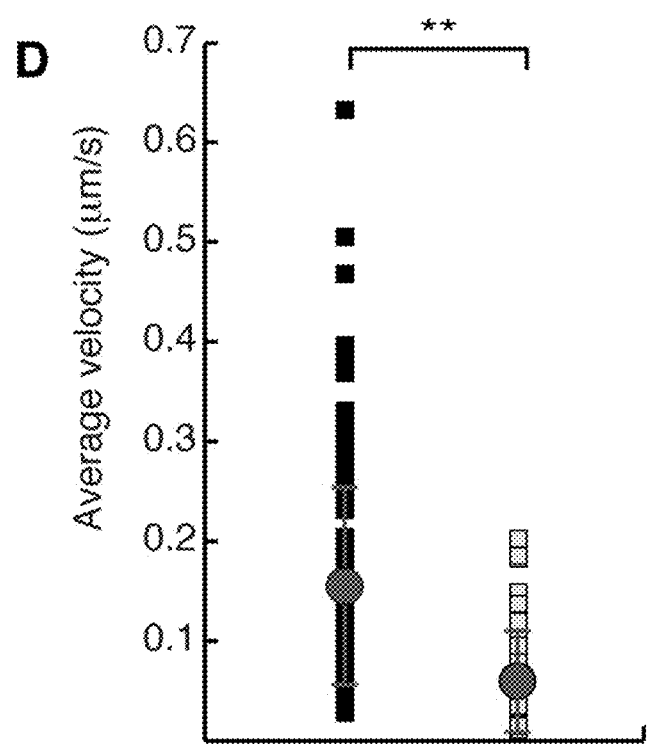
FIG. 6D shows a scatter plot of the average velocity of moving mitochondria, in which the red dots indicate the population averages±SD; the statistical significance was calculated as in FIG. 2C (n=138 mitochondria in heterozygous slices, n=38 mitochondria in mutant slices), and the scale bar represents 5 µm for all images, according to embodiments of the present invention.

To monitor mitochondrial transport along dopaminergic axons and dendrites, live imaging of mito-Dendra2 was performed in the slice cultures. For accurate monitoring of mitochondrial dynamics in the dense milieu of dopaminergic projections, mitochondria were photo-converted in a nerve process and tracked the movement of this labeled subpopulation (FIG. 6A, top). From the time-lapse movies, kymograph representations were generated that resolved the complex trajectories of the photo-converted mitochondria (FIG. 6A, bottom). With a vertical time axis, mobile mitochondria create diagonal tracks, whereas stationary mitochondria project as vertical streaks. Consistent with previous studies describing the mobility of mitochondria in neuronal processes, it was found that a subpopulation of mitochondria is highly mobile in control dopaminergic neurons (FIG. 6A). In contrast, mitochondrial transport is minimal in Mfn-null neurons (FIG. 6B). In heterozygous controls, 50% of photo-conversion experiments resulted in at least one transport event, defined as directed movement for 5 µm. In Mfn2 mutants, only 14% of photo-conversion experiments showed a transport event (FIG. 6C). Additionally, mobile mitochondria in mutant dopaminergic neurons exhibit more intermittent movements and longer immobile periods. As a result, the average velocity for mitochondria in Mfn2-null slices is also slower relative to controls, 0.05 µm/s versus 0.15 µm/s (FIG. 6D).

Example 6

Rescue of Mfn2 Mutants with L-DOPA Treatment

Figure 7A:
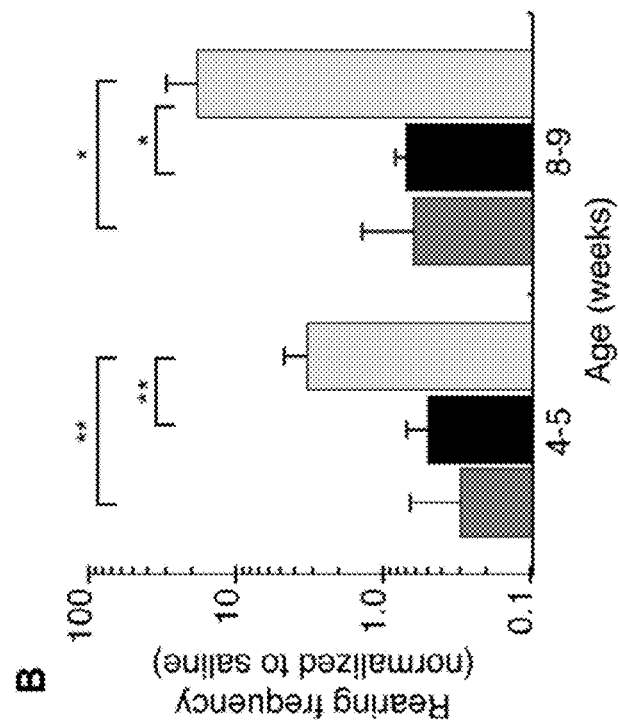
FIG. 7A distance traveled in an open field after L-DOPA injection, in which animals as indicated were analyzed by an open field test after a control saline injection to obtain baseline activity, and were then tested a second time after an L-DOPA injection, where for each animal, the activity after L-DOPA treatment was normalized to the activity after the saline injection, and the Student t-test was used to obtain p-values (* $p<0.05$; ** $p<0.001$; n=10-15 per genotype), with error bars representing propagated error, according to embodiments of the present invention.
Figure 7B:
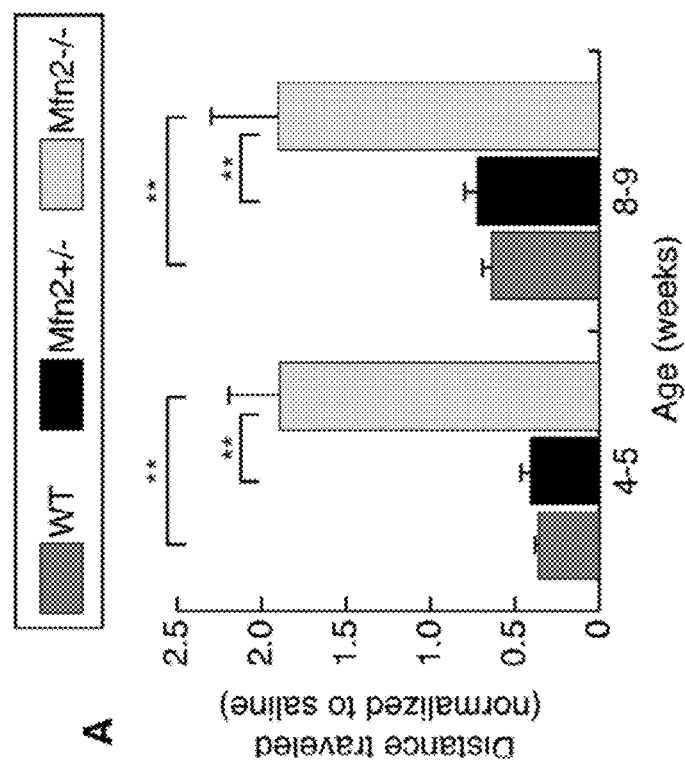
FIG. 7B shows rearing frequency after L-DOPA injection performed as described in FIG. 7A, according to embodiments of the present invention.

The reduced level of TH-positive terminals in Mfn2 mutant mice implies a deficiency of dopamine in the striatum. Therefore, it was tested whether administration of L-DOPA by peritoneal injection could alleviate the motor defect of Mfn2 mutant mice. With 4-5 week and 8-9 week old mice, it was found that L-DOPA administration caused a substantial increase in both the travel distance as well as the rearing frequency of Mfn2 mutant mice (FIG. 7).

Several genes associated with familial PD—including PINK1, Parkin, DJ-1, and LRRK2—have been linked to mitochondrial dynamics. In order to understand the role of mitochondrial dynamics in the nigrostriatal pathway, the mitofusins Mfn1 and Mfn2 were deleted from a subset of dopaminergic neurons, including those of the SNc. Mfn2 mutants exhibit severe locomotive defects, which are preceded by the loss of dopaminergic efferents to the striatum. These mice show dysfunction of the dopaminergic circuit in the striatum and motor deficits weeks earlier than the loss of nigral neurons. This sequence of pathological findings is consistent with retrograde degeneration, in which neuronal deficits initiate distally in the axon terminals and progress backwards to the cell bodies. Interestingly, pathological studies of PD brains have suggested a similar "dying back" mode of neurodegeneration based on the disproportionate loss of striatal dopamine relative to the neuronal loss in the SNc, as described in Hornykiewicz, O., 1998, *Neurology*, 51, S2-9, and Cheng, H. C., et al, 2010, *Ann Neurol*, 67, 715-725, the entire contents of both of which are herein incorporated by reference. Administration of MPTP (1-methyl-4-phenyl-1,2,3,6-tetrahydropyridine) to rhesus monkeys also produces this differential pattern of neuronal damage, as described in Pifl, C. et al., 1991, *Neuroscience*, 44, 591-605, the entire contents of which are herein incorporated by reference.

It was found that dopaminergic neurons lacking Mfn2 have a prominent defect in mitochondrial content and transport in neuronal processes. This latter observation supports growing evidence that the mitofusins are important for mitochondrial movement, as described in Chen, H. et al., 2003, *The Journal of Cell biology*, 160, 189-200, and Misko, A. et al., 2010, *The Journal of Neuroscience*, 30, 4232-4240, the entire contents of both of which are herein incorporated by reference.

The identification of PD-related genes, such as α-synuclein, PINK1, Parkin, DJ-1, and LRRK2, has led to the development of numerous mouse models of PD. Although some of these models show modest decreases of striatal dopamine and associated motor impairments, they generally fail to recapitulate the progressive loss of dopaminergic neurons that is the pathological hallmark of PD. In contrast, disruption of mitochondrial function by loss of mitochondrial transcription factor A (Tfam) results in dopamine cell death. Loss of Tfam results in reduced mitochondrial DNA content and severe respiratory chain deficiency. Herein, it is found that dopaminergic neurons lacking the mitochondrial fusion gene Mfn2 exhibit fragmented mitochondria that fail to be transported within the axon. The presently disclosed mouse model is a demonstration of progressive degeneration at the cellular level. Early deficits are regionally restricted to the nerve terminals, and it takes two months to progress to neuronal cell loss. The time span between distal defects and cell loss presents a window for investigating the cellular mechanisms leading to degeneration of dopaminergic neurons.

Example 7

Generation of Mfn Mutant Mice

Conditional mouse lines of Mfn1 and Mfn2 have been previously described in Chen, H. et al., 2007, *Cell*, 130, 548-562, the entire contents of which are herein incorporated by reference. The Slc6a3-Cre driver was obtained from the Jackson Laboratory (B6. SJL-Slc6a3tm1.1 (cre)Bkmn/J). All experiments were approved by the Caltech Institute Animal Care and Use Committee.

Example 8

Open Field Test

Animals were placed in a 50 cm×50 cm white Plexiglass box and allowed an adaptation period of 30-60 minutes prior to being analyzed. Activity was recorded for two consecutive sessions, each lasting 15 minutes, by a ceiling-mounted video camera. The Ethovision software (Noldus, Leesburg, Va.) was used to measure the distance, velocity, rearing frequency, and immobility of the mice.

In the L-DOPA experiments, animals were first injected intraperitoneally with saline and monitored by open field analysis to obtain baseline activity. Subsequently, animals were administered a cocktail of L-3,4-dihydroxyphenylalanine methyl ester (25 mg/kg, Sigma) and the DOPA decarboxylase inhibitor benserazide hydrochloride (5 mg/kg, Sigma). After 60 minutes, animals were followed by open field analysis.

Example 9

Histological Analysis

Animals were sacrificed after anesthesia with halothane. Brains were dissected and fixed overnight at 4° C. in 10% neutral buffered formalin. The caudal portions of the brains were trimmed in an acrylic matrix (2 mm from the end) before specimens were mounted and sectioned with the Leica VT1200S vibratome. Brains were sliced into consecutive sections of 50 µm for the striatum or 35 µm for the midbrain. For counting, every 4$^{th}$ midbrain slice was processed for TH (1:1000, Chemicon) immunohistochemistry following the manufacturer's protocol (Vectastain elite ABC kit, Vector Labs). To enhance antigenicity, slides were boiled for 40 min in 10 mM sodium citrate buffered at pH 6. Sections were developed with 3,3'-diaminobenzidine and subsequently immersed in a 0.1% cresyl violet acetate solution for Nissl counterstain. Each slide contained a set of homozygous, heterozygous, and wildtype samples to minimize staining variability between samples. Two reviewers, blinded to the genotypes, counted TH-immunoreactive and Nissl-positive cells at 100× magnification. For each animal, 9 sections spanning the midbrain were counted. Total counts from the heterozygotes and homozygotes were normalized to the age-matched wildtype controls. Densitometry was performed on the TH signal in the striatum. Briefly, the Nikon Elements software was used for computer-assisted measurement of TH intensity in the striatal area. The same threshold was maintained across all samples on the slide. For each animal, 3 sections, spanning the rostral-caudal extent of the striatum, were measured, summed, and normalized to wildtype measurements.

For Nissl staining, sections were stained with Nissl conjugated Alexa 633 (1:500, Molecular Probes) for 1 hour at RT. Sections were rinsed with several times with PBS prior to mounting with Cytoseal.

Example 10

Imaging and Microscopy Analysis

Images were acquired on a Zeiss LSM 710 confocal microscope using EC-Plan-Neofluar 40×/1.3 oil or Plan-Apochromat 63×/1.4 oil objectives. Z-stack acquisitions oversampled twice the thickness of the optical slice, and Zen 2009 analysis software was used for maximum z-projections. To photo-convert Dendra2, a small region was irradiated with the 405 nm laser (4% laser power) for 60 iterations at a scan speed of 6.3-12.61 µs/pixel. For live imaging, slices were submerged in Tyrode's buffer (Sigma) supplemented with 25 mM HEPES and 6.5 mg/ml glucose and stabilized with a slice anchor (Warner Instruments). Slices were imaged on a stage-top heated platform maintained at 35° C. Four fields were imaged in each slice and time-lapse movies were acquired at 20 s intervals for 15 minutes. Custom macros were written for ImageJ software to produce kymographs and to measure velocity traces. In quantifying mitochondrial area, noise reduction in maximally z-projected images utilized the median and Liptschitz top hat filters. Subsequently, the dynamic thresholding plugin was applied to segment mitochondria, and the Analyze particles algorithm in ImageJ provided quantitation of mitochondrial signal. Manual counts of mito-Dendra2-positive cells in the z-stacks used the Cell counter algorithm.

Example 11

Organotypic Slice Cultures

Preparations of sagittal organotypic slices have been described in Hornykiewicz, O. 1998, supra. Modifications were made to the angle of sectioning to improve preservation of nigrostriatal projections (Beurrier et al., 2006, supra). The rotating magnetic stage from the Leica VT1200S vibratome was tilted so that sections could be acquired between 10-15° from the midline. Pups were sacrificed at postnatal day 10-12. Typically, only two slices (one per hemisphere) of 330 µm thickness contained the nigrostriatal pathway. Slices acquired at 1-1.2 mm lateral from the midline were retained for culturing. Cultures were fed 3 times a week using Stoppini media (Cheng et al., 2010, supra). Brain slices were equilibrated in culturing conditions for at least 2 weeks prior to experimentation. For immunofluorescence, membranes around the slices were trimmed and fixed in 4% paraformaldehyde-lysine-periodate overnight at 4° C. Slices were permeabilized with 1% Triton X-100 for 30 minutes and incubated with blocking buffer (2% goat serum, 1% BSA, and 0.1% Triton-X100) for 4-6 hours at room temperature. Samples were incubated with anti-TH antibody overnight at 4° C., followed by secondary antibody (goat anti-rabbit IgG Alexa 568, Molecular Probes) for 2 hours.

Example 12

Visualization of Mitochondrial Defects in Purkinje Neurons Lacking Mfn2

Figure 10:
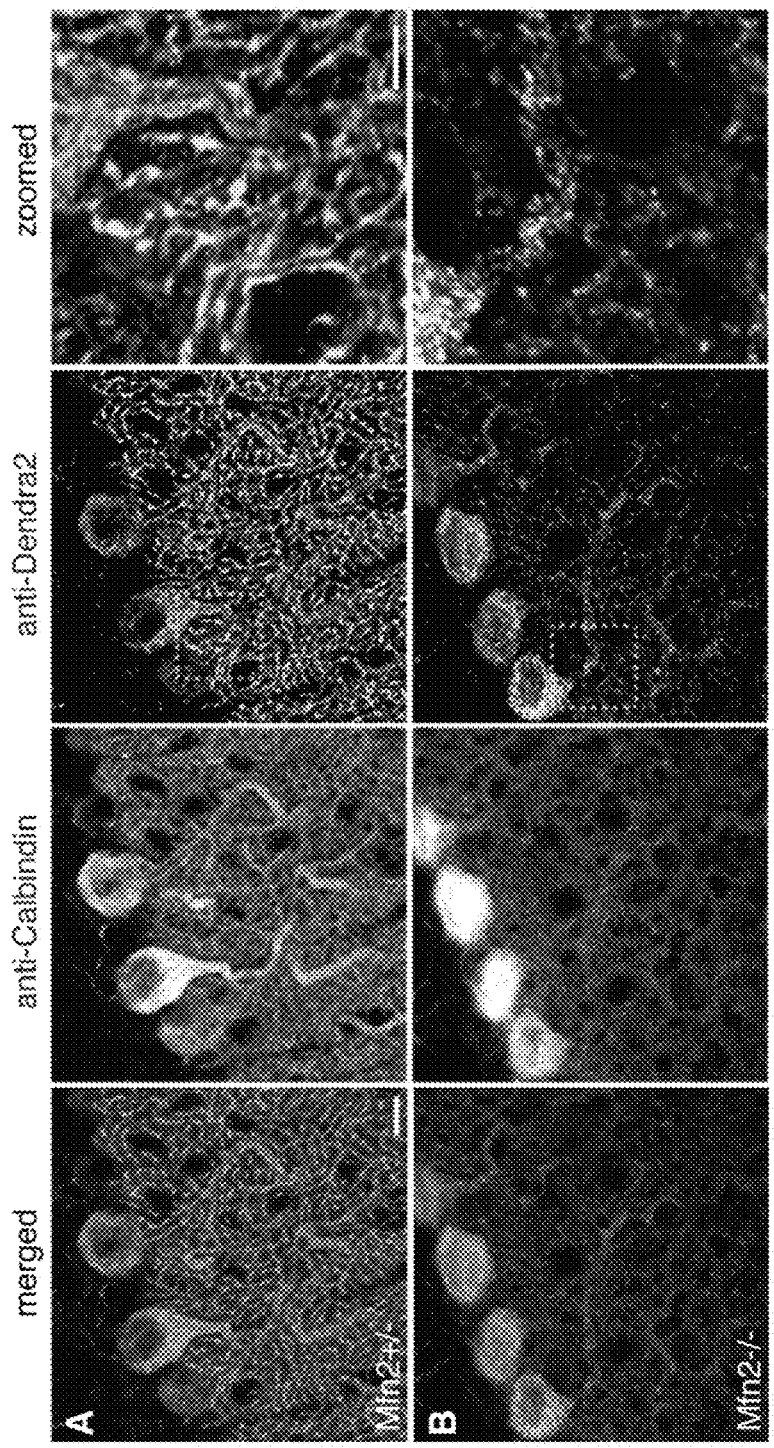
FIG. 10 shows visualization of mitochondrial defects in Purkinje neurons lacking Mfn2, in which the top row of images show normal wildtype Purkinje neurons and the bottom row of images show Purkinje neurons disrupted at the Mfn2 locus using a Pcp2-Cre expression system, according to embodiments of the present invention.

Frozen sections of cerebellum were stained for calbindin (red) and Dendra (green), as shown in FIG. 10. The top row of images are from a control mouse with normal Purkinje neurons, and the bottom row of images is from a littermate lacking Mfn2 in Purkinje neurons due to the Pcp2-Cre driver (Jackson Laboratory, Bar Harbor, Me.). The "zoomed" images show high magnification of the boxed regions as indicated in FIG. 10. The scale bar represents 10 µm in the merged image and 5 um in the magnified image (101×54 mm; 300×300 DPI).

As disclosed throughout, an animal model for Parkinson's disease is provided in which the Mfn2 gene is disrupted in dopaminergic neurons.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A transgenic mouse having a genome comprising a homozygous disruption of the endogenous Mfn2 gene expression in the dopaminergic neurons, wherein the transgenic mouse exhibits locomotive defects compared to a mouse having a wildtype Mfn2 genotype.

2. The transgenic mouse of claim 1, wherein the homozygous disruption of the endogenous Mfn2 gene expression comprises a nucleic acid sequence inserted within the endogenous Mfn2 gene.

3. The transgenic mouse of claim 2, wherein the nucleic acid sequence encodes for a photo-activatable fluorescent protein that is capable of targeting mitochondria.

4. The transgenic mouse of claim 1, wherein the locomotive defects comprise bradykinesia and/or postural defects.

5. The transgenic mouse of claim 1, wherein the transgenic mouse has decreased dopaminergic innervation compared to a mouse having a wildtype Mfn2 genotype.

* * * * *